(12) United States Patent  
Haghighi-Mood

(10) Patent No.: US 6,735,466 B1  
(45) Date of Patent: May 11, 2004

(54) ANALYTICAL SIGNAL METHOD FOR ANALYSIS OF T-WAVE ALTERNANS

(75) Inventor: Ali Haghighi-Mood, Andover, MA (US)

(73) Assignee: Cambridge Heart, Inc., Bedford, MA (US)

( * ) Notice: Subject to any disclaimer, the term of this patent is extended or adjusted under 35 U.S.C. 154(b) by 473 days.

(21) Appl. No.: 09/672,034

(22) Filed: Sep. 29, 2000

Related U.S. Application Data

(60) Provisional application No. 60/156,524, filed on Sep. 29, 1999.

(51) Int. Cl.[7] ............................................. A61B 5/0452
(52) U.S. Cl. ....................................... 600/515; 600/516
(58) Field of Search ................................. 600/509, 515, 600/516, 544, 546; 607/25

(56) References Cited

U.S. PATENT DOCUMENTS

| | | | |
|---|---|---|---|
| 4,802,491 A | | 2/1989 | Cohen et al. ............... 600/515 |
| 5,437,285 A | * | 8/1995 | Verrier et al. ............... 600/518 |
| 5,570,696 A | | 11/1996 | Arnold et al. .............. 600/520 |
| 5,704,365 A | | 1/1998 | Albrecht et al. ............ 600/515 |

OTHER PUBLICATIONS

Smith JM, Clancy EA, Valeri CR et al. "Electrical alternans and cardiac electrical instability". Circulation 1988; 77: 110–121.*

Adam Dr, Smith JM, Akselrod S. et al. "Fluctuations in T–Wave morpnology and susceptibility to ventricular fibrillation". Journal of Electrocardiology (London), 1984; 17:209–218.*

S. Lawrence Marple, Jr.; "Computing the Discrete–Time 'Analytic' Signal Via FFT"; *Asilomar Conference on Signals, Systems and Computers*, US, Los Alamitos, CA IEEE; Nov. 2, 1997; pp. 1322–1325.

O. Fokapu et al.; "A New Approach For P Wave Detection Using Analytic Signal"; *Proceedings of the Annual International Conference of Engineering in Medicine and Biology Society*, US, New York, IEEE vol. Conf. 15; Oct. 28, 1993; pp. 400–401.

Mustafa A. Murda'H et al.; "Repolarization Alternans: Techniques, Mechanisms, and Cardiac Vulnerability"; *PACE—Pacing and Clinical Electrophysiology*, Futura Publishing Company, Inc., US; vol. 20, No. 10, Part 02; Oct. 1, 1997; pp. 2641–2657.

* cited by examiner

*Primary Examiner*—Carl Layno  
(74) *Attorney, Agent, or Firm*—Fish & Richardson P.C.

(57) ABSTRACT

Alternans is measured in a physiological signal, such as an electrocardiogram, by processing the physiological signal to create a processed signal having an asymmetric spectrum, and processing the processed signal to measure alternans in the physiologic signal. The physiological signal may be processed to produce an analytical signal by converting the signal to the frequency domain, removing components corresponding to negative frequencies, and converting back to the time domain.

29 Claims, 6 Drawing Sheets

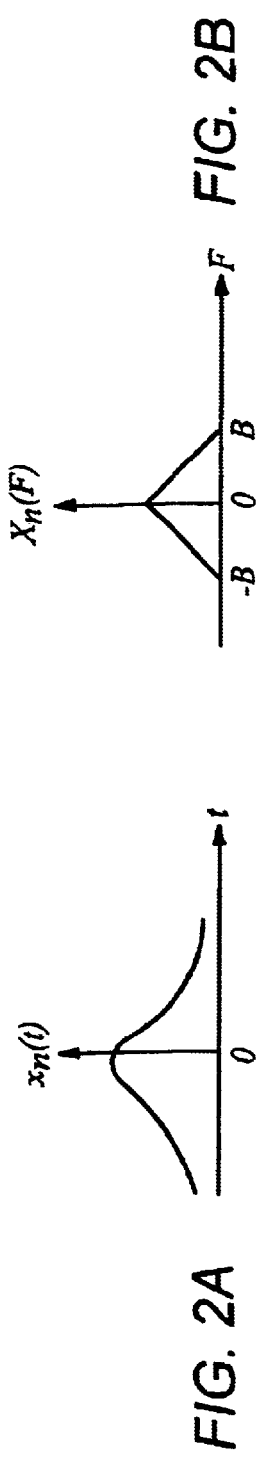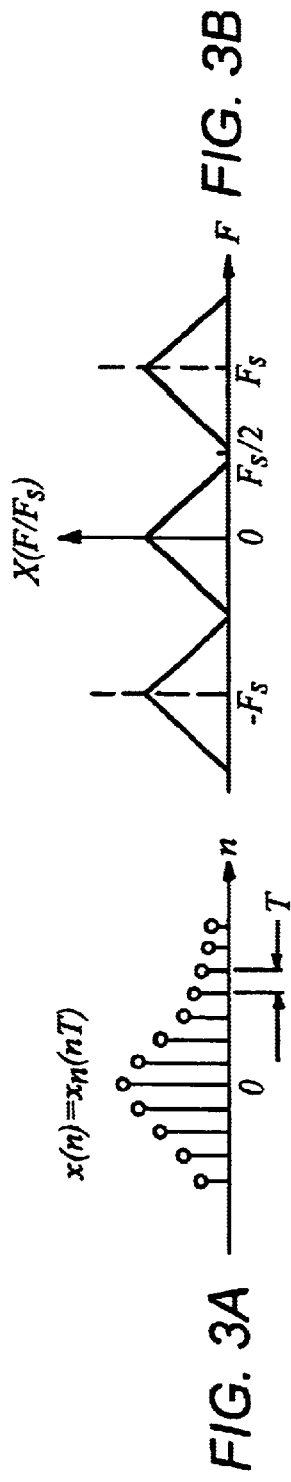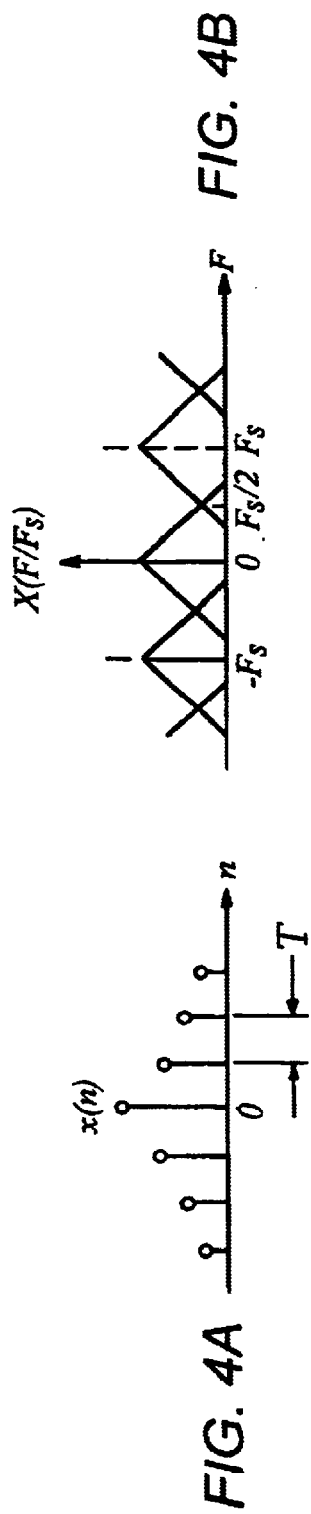

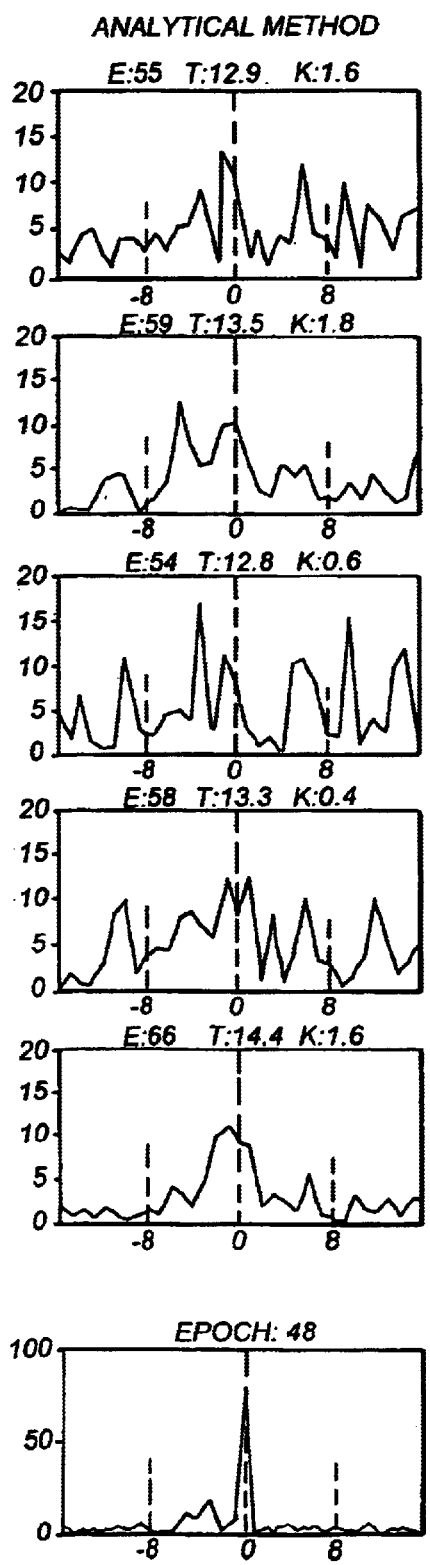
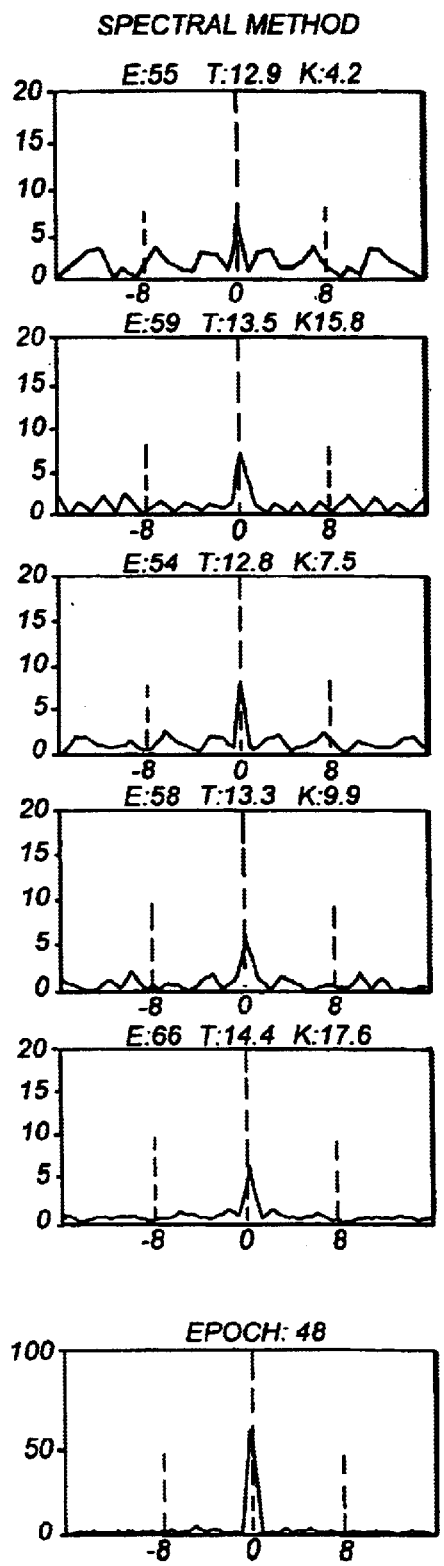
FIG. 11A
FIG. 11B

US 6,735,466 B1

ANALYTICAL SIGNAL METHOD FOR ANALYSIS OF T-WAVE ALTERNANS

This application claims the benefit of Provisional application Ser. No. 60/156,524, filed Sep. 29, 1999.

TECHNICAL FIELD

The invention is directed to techniques for measuring alternans in an electrocardiogram (ECG) waveform.

BACKGROUND

Alternans, a subtle beat-to-beat change in the repeating pattern of an (ECG) waveform can be indicative of electrical instability of the heart and increased susceptibility to sudden cardiac death. Alternans results in an ABABAB . . . pattern of variation of waveform shape between successive beats in an ECG waveform. The level of variation has been found to be a useful characterization of an individual's cardiac electrical stability, with increasing variation being indicative of decreasing stability.

Referring to FIG. 1, an ECG waveform for a single beat is typically referred to as a PQRST complex. Briefly, the P wave appears at initiation of the beat and corresponds to activity in the atria, while the QRST complex follows the P wave and corresponds to ventricular activity. The QRS component represents the electrical activation of the ventricles, while the T wave represents their electrical recovery. The ST segment is a relatively quiescent period. It has been found that the T wave is the best interval of the ECG complex for detecting alternans. That is, a level of variation in the T waves of alternating beats is the best indicator of the electrical stability of the ventricles—the heart's main pumping chambers.

While an ECG waveform typically has a QRS amplitude measured in millivolts, an alternans pattern of variation with an amplitude on the order of a microvolt may be clinically significant. Accordingly, the alternans pattern may be too small to be detected by visual inspection of the electrocardiogram and often must be detected and quantified electronically. Such electronic detection and quantification of the alternans pattern is further complicated by the presence of noise in the ECG waveforms, as the noise may result in beat-to-beat variations that have a larger magnitude than the alternans pattern of variation.

The noise in an ECG signal can be classified into three categories: baseline noise generated in the electrode, physiologic noise, and external electrical noise. The baseline noise is low frequency noise that appears as an undulating baseline upon which the ECG rides. Baseline noise is attributable to motion and deformation of the electrode, and results from low frequency events such as patient respiration and patient motion. As a result, the magnitude of baseline noise tends to increase with exercise. Typically, the frequency content of baseline noise is below 2 Hz.

Physiologic noise results from physiologic processes, such as skeletal muscle activity, that interfere with the ECG signal. The electrical activity of the skeletal muscles creates potentials that are additive with respect to the potentials created by the heart. The frequency content of the skeletal muscle signals is comparable to the frequency content of the QRS complex, and is typically greater than 10 Hz. When measuring T-wave alternans, additional physiologic noise may result from changes in the position of the heart due to respiration or from changes in the projection of the electrical potential from the heart to the skin surface due to thoracic conductivity changes arising from the inflation and deflation of the lungs with respiration.

External electrical noise results, for example, from ambient electromagnetic activity in the room, electrode cable motion, and variations in amplifiers or other components of the ECG circuitry. External electrical noise may be eliminated or reduced through the use of high quality components and through the reduction of ambient electromagnetic activity by, for example, deactivating high power equipment.

Noise in the ECG waveform also can mimic the presence of alternans where none exists. For example, if a patient is breathing at one half or one third of the heart rate, the respiration may introduce a harmonic signal having the ABABAB . . . pattern of alternans. Motion that repeats with some periodicity, such as that resulting from exercise, can create electrode noise with a similar pattern.

One alternans measurement approach that attempts to address the effects of noise is referred to as the spectral method for measuring T-wave alternans. This method is described in detail in U.S. Pat. No. 4,802,491, which is incorporated by reference. In summary, this method involves concurrently analyzing 128 beats of a continuous stream of ECG signals. The spectral method uses measurements from time synchronized points of consecutive T waves. A time series is created by measuring, for each of the 128 beats, the T-wave level at a fixed point relating to the QRS complex. This process is repeated to create a time series for each point in the T wave. A frequency spectrum is then generated for each time series, and the spectra are averaged to form a composite T-wave alternans spectrum. Since the T-waves are sampled once per beat for each time series, the spectral value at the Nyquist frequency, i.e. 0.5 cycle per beat, indicates the level of beat-to-beat alternation in the T-wave waveform.

The alternans power is statistically compared to the noise power to discriminate the beat-to-beat T-wave variation due to abnormal electrical activity of the heart from the random variation due to background noise. The alternans power is calculated by subtracting the mean power in a reference band used to estimate the background noise level (for example, the frequency band of 0.44–0.49 cycle per beat) from the power at the Nyquist frequency (0.50 cycle per beat). Alternans is considered to be significant if the alternans is at least three times the standard deviation of the noise in the noise reference band.

SUMMARY

The invention provides improved techniques for measuring T-wave alternans.

The spectral method for T-wave alternans measurement relies on two assumptions. The first assumption is that the physiological T-wave alternans is phase-locked with the T-wave and therefore can be sampled at a constant phase in every beat. This assumption is valid due to the physiological factors associated with the generation of T-wave alternans.

The second assumption is that the noise within the noise reference band is white. To satisfy this condition, colored noise (e.g., motion artifact due to exercise) must be avoided within the noise reference band. During an ergometer exercise test, the pedaling rate can be adjusted to ⅓ or ⅔ of the heart rate using auditory and visual cues to move most of the colored noise away from the noise reference band and the alternans frequency. Nonetheless, colored noise often can fall within the noise reference noise band and at the alternans frequency during ergometer exercise due to the exercise, other motion artifact, respiration, and other sources. Furthermore, during treadmill exercise, it is difficult to control the stepping rate and it is common for the exercise-induced motion artifact to create colored noise that falls within the noise reference band and at the alternans frequency.

In one general aspect, measuring alternans in a physiological signal includes processing the physiological signal to create a processed signal having an asymmetric spectrum (i.e., a spectrum that is asymmetric around DC), and processing the processed signal to measure alternans in the physiologic signal.

Processing the physiological signal to create a processed signal may include creating the processed signal as an analytical signal, or as an approximation of an analytical signal. Creating an analytical signal may include generating a frequency domain representation of the physiological signal, modifying the frequency domain representation to remove components corresponding to negative frequencies, and generating the analytical signal as a time domain representation of the modified frequency domain representation.

The physiological signal may be an electrocardiogram. The electrocardiogram may be recorded from a subject during exercise, such as exercise using an ergometer or a treadmill.

Processing the processed signal may include sampling the processed signal at a frequency less than or equal to twice a frequency corresponding to alternans. For example, the processed signal may be sampled once per beat, where the frequency of alternans is once every other beat. Stated another way, processing involves processing samples of the signal spaced by intervals greater than or equal to half the period of alternans.

In another general aspect, alternans may be measured using a system having an input unit configured to receive the physiological signal, a processor, and an output unit. The processor is connected to the input unit and configured to process the physiological signal to create a processed signal having an asymmetric spectrum, and to process the processed signal to generate an indication of alternans in the physiologic signal. The output unit is connected to the processor and configured to receive and output the indication of alternans.

In another general aspect, a band-limited signal may be analyzed by producing an analytical signal version of the signal, sampling the analytical signal, and processing samples of the signal spaced by intervals greater than or equal to half the period of the highest frequency component of the band-limited signal to produce a sampled analytical signal, and analyzing the sampled analytical signal.

The band-limited signal may be a physiological signal, such as an electrocardiogram, and the analysis may involve measurement of alternans. The band-limited signal also may be an electro-encephalogram signal.

When the band-limited signal is periodic, the analysis may include detecting frequency components which are located at or near submultiples of the reciprocal of the period of the band-limited signal.

Other features and advantages will be apparent from the following description, including the drawings, and from the claims.

DESCRIPTION OF DRAWINGS

FIGS. 2A and 2B are graphs of, respectively, a band-limited signal and the power spectrum of the signal.

FIGS. 3A and 3B are graphs of, respectively, the band-limited signal of FIG. 2A sampled at a frequency greater than twice the frequency of the highest frequency component of the band-limited signal, and the corresponding power spectrum for the sampled signal.

FIGS. 4A and 4B are graphs of, respectively, the band-limited signal of FIG. 2A sampled at a frequency less than twice the frequency of the highest frequency component of the band-limited signal, and the corresponding power spectrum for the sampled signal.

FIGS. 11A and 11B are graphs of power spectra generated using, respectively, an analytical signal approach and the spectral method.

DETAILED DESCRIPTION

Figure 1:
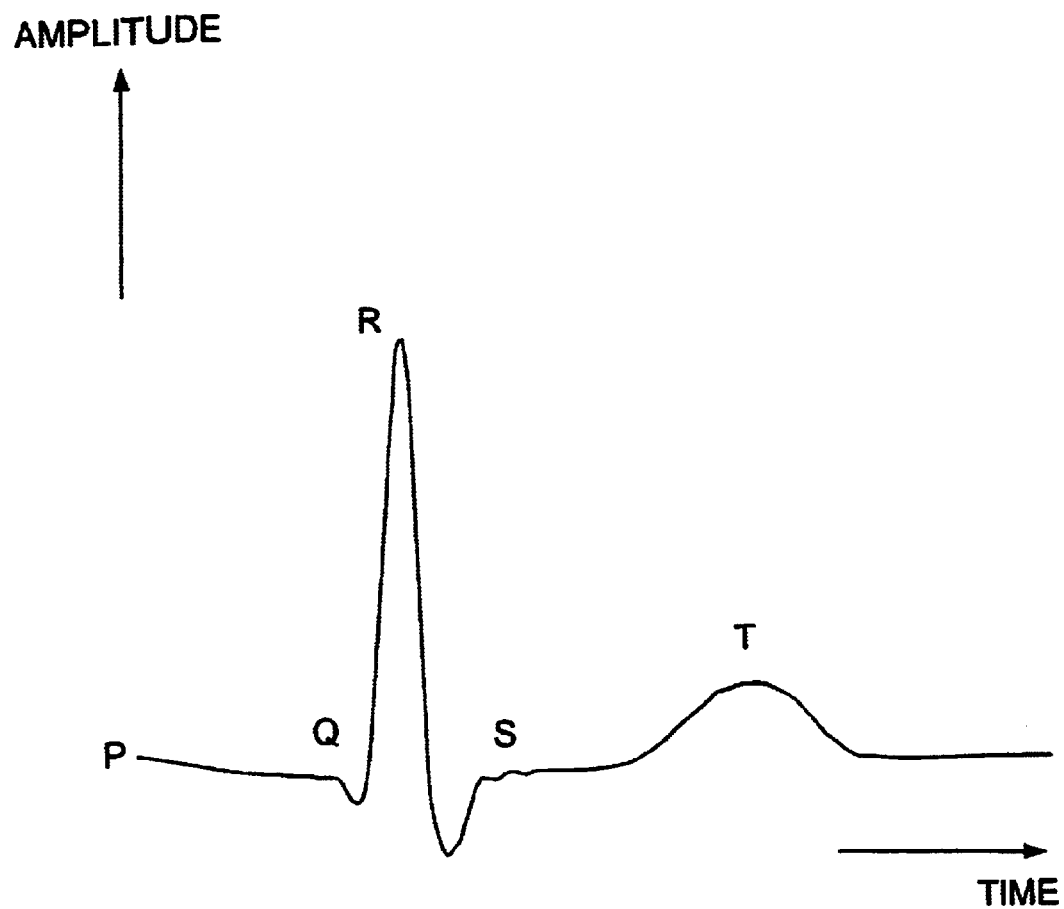
FIG. 1 is a graph of an ECG waveform for a single beat.

Techniques are described for processing an ECG signal to reduce or eliminate the effect of colored noise. Detection of alternans in an ECG signal may be improved by processing the ECG signal to reduce or eliminate the effects of noise. However, in processing a signal that includes colored noise, errors may result if one assumes that the noise is white.

Theoretically, to avoid aliasing when sampling a signal at a given rate, $F_s$, the signal must be band limited to half of the sampling frequency, $0.5F_s$, which is referred to as the Nyquist frequency.

FIGS. 2A and 2B show, respectively, a band-limited analog signal $x_a(t)$ and the power spectrum $X_a(f)$ for that signal. Note that the power spectrum is symmetric about zero.

When the analog signal is sampled, the spectrum for the sampled signal is periodic with a period equal to the sampling frequency, $F_s$. FIGS. 3A and 3B show a case in which the sampling frequency is greater than twice the signal bandwidth, 2B. As shown, there is no interference between adjacent spectral periods, and, accordingly, an accurate measurement of signal power at all frequencies of the original analog signal can be made by considering the spectrum for a spectral period.

FIGS. 4A and 4B show a case in which the sampling rate is smaller than 2B. As shown, interference between adjacent spectral periods distorts the spectrum for the frequencies of overlap.

As shown in FIGS. 4A and 4B, failure to comply with the Nyquist requirement (i.e., use of a sampling frequency smaller than twice the signal bandwidth) results in under-estimation of signal power at all overlapped frequencies including the Nyquist frequency. For alternans detection, the sampling rate is limited to one sample per beat and, since the alternans frequency is at exactly the Nyquist frequency, the signal cannot be band limited to comply with the Nyquist requirement.

The spectral method for T-wave alternans measurement is an accurate method in the case of T-wave alternans measured during exercise tests performed on an ergometer with the pedaling rate well controlled at ⅓ or ⅔ of the heart rate. This is because two conditions tend to reduce or eliminate the effects of failure to comply with the Nyquist requirement.

First, the noise within the noise band can be considered to be white. Since the spectrum for white noise is flat for all frequencies, there is interference from multiple adjacent spectral cycles. This, in turn, means that interference due to noise is statistically equivalent for all frequencies.

Second, as noted above, the alternans is phased-locked (i.e. the ECG signal is sampled at synchronized points). This means that the signals at the Nyquist frequency interfere with consistent phase, which results in a correct estimation of signal power at this frequency.

Colored noise artifacts may occur in T-wave alternans measured during ergometer exercise. For example the pedaling rate may not be well controlled, or the artifact due to respiration may cause colored noise to occur in the noise band and at the alternans frequency.

Figure 5A:
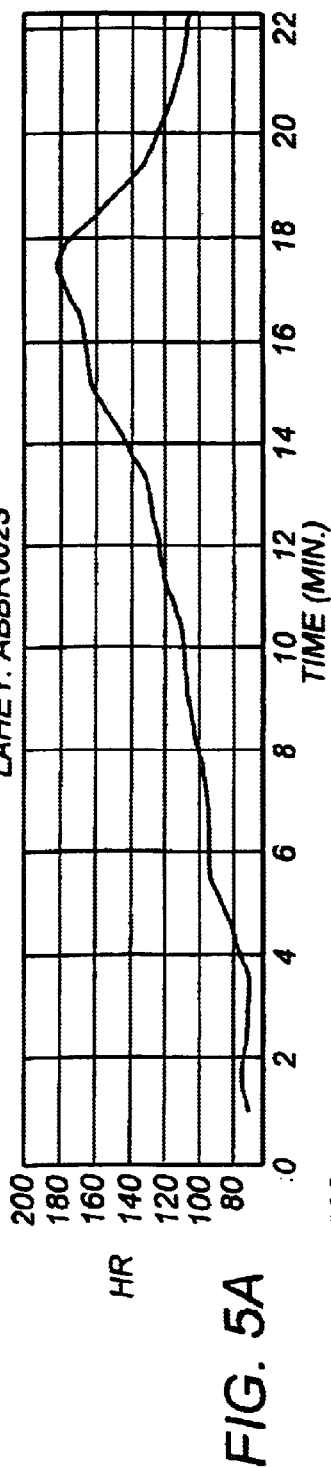
FIG. 5A is a plot of the heart rate of a patient versus time during a treadmill exercise test.
Figure 5B:
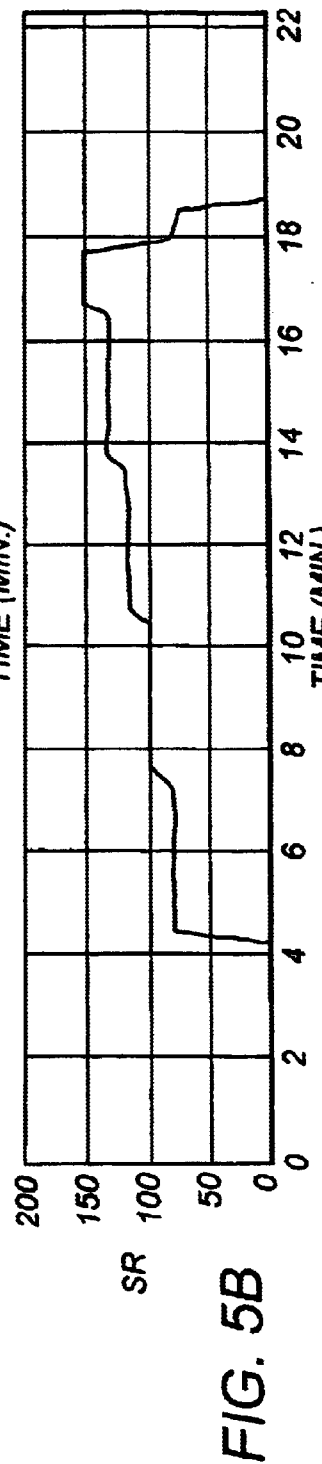
FIG. 5B is plot of the stepping rate of the patient versus time.
Figure 5C:
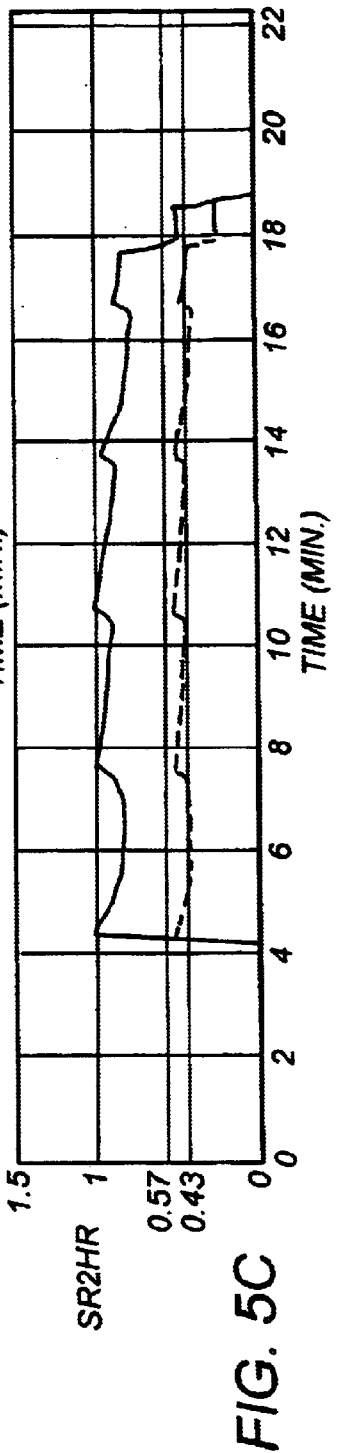
FIG. 5C is a plot of the stepping rate divided by the heart rate (solid line) and the first sub-harmonic of the stepping rate divided by the heart rate (dotted line).

Colored noise may also exist for tests using treadmill exercise. With such exercise, motion artifact due to walking/ running may produce unwanted signals of colored nature at or close to the alternans frequency. In treadmill exercise tests, the walking rate is generally close to the heart rate such that sub-harmonics of the heart rate may create significant noise components within the noise band. FIGS. 5A–5C show a typical treadmill exercise test case in which the patient's stepping rate is close to the heart rate. FIG. 5A shows the heart rate as a function of time, FIG. 5B shows the stepping rate, and FIG. 5C shows the stepping rate and its sub-harmonic, normalized to the heart rate. In this particular case, the stepping creates artifacts at frequencies close to half of the heart rate.

In a case such as is illustrated in FIGS. 5A–5C, since the noise within the noise band is colored, interference between components from adjacent spectra of different phase results in underestimation of noise and therefore overestimation of alternans power, which in turn may produce false positive results for treadmill T-wave alternans tests.

Figure 6:
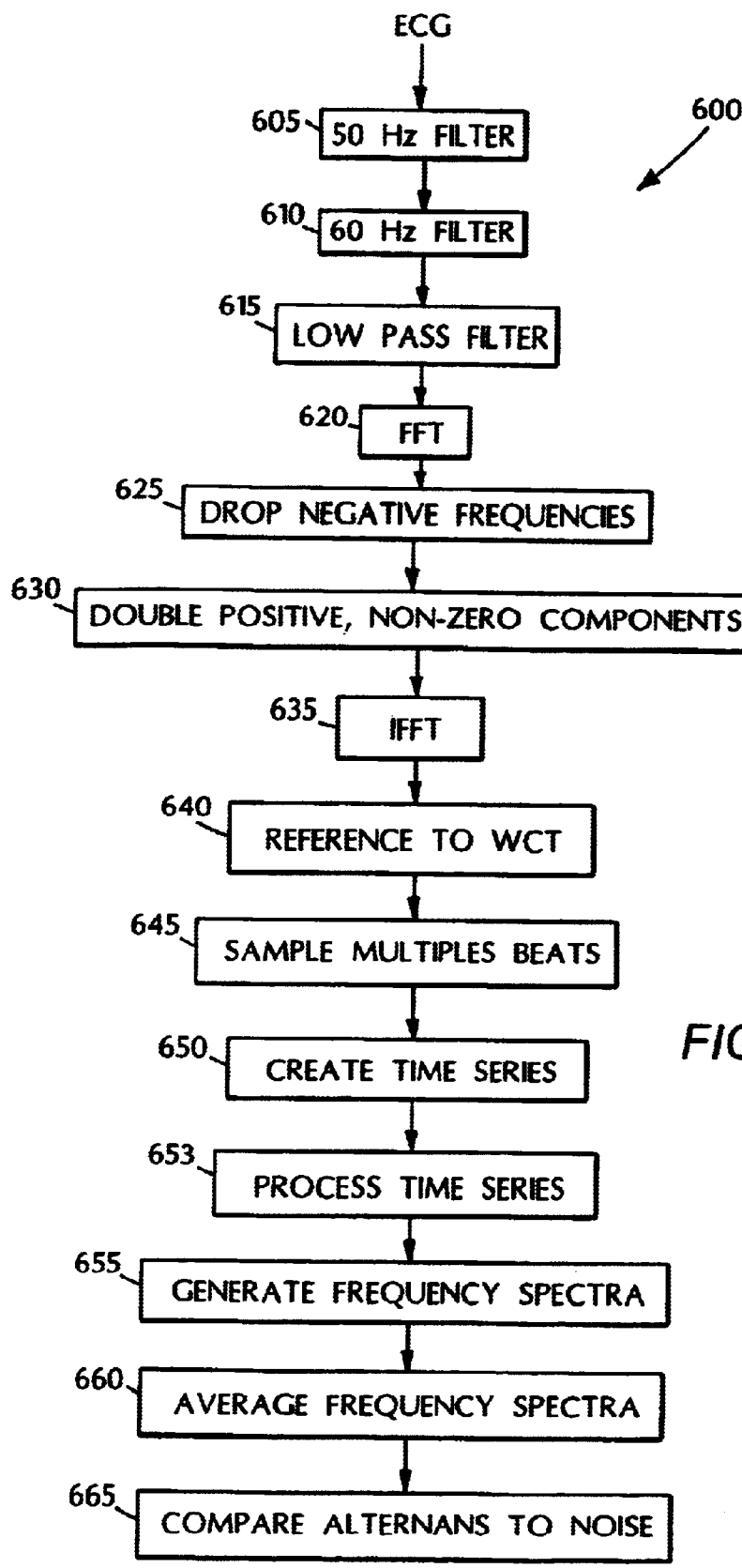
FIG. 6 is a flow chart of a procedure for processing ECG signals.

Referring to FIG. 6, problems associated with the presence of colored noise may be avoided through use of an analytical signal technique 600. According to the technique 600, an ECG signal is processed using a 50 Hz filter (step 605) and a 60 Hz filter (step 610). This processing reduces the effects of line voltages used to power the equipment that generates the ECG signal, with 60 Hz being the standard line voltage frequency in the U.S. and 50 Hz being standard in Europe.

Next, an analytical version of the signal is created (steps 615-635). First, the signal is low-pass filtered (step 615). In one implementation, the low pass filter is a $5^{th}$ order Butterworth filter with a zero phase configuration. The filtered signal is then transferred to the frequency domain using a fast Fourier transform (FFT) (step 620).

In the frequency domain, the portions of the frequency spectrum corresponding to negative frequencies are removed (step 625). The technique then compensates for removal of negative frequencies by doubling all positive, non-zero components of the frequency spectrum (step 630). An inverse fast Fourier transform (IFFT) is then performed on the modified frequency spectrum to produce an analytical signal in the time domain (step 635).

Next, the analytical signal is referenced to an analytical version of Wilson's central terminal (step 640). Wilson's central terminal (WCT) is a well-known ECG reference value. The analytical version of WCT is generated from the standard WCT using the procedure set forth in steps 615–635. The analytical signal is referenced to the analytical version of WCT by determining the difference between the two signals.

The referenced analytical signal then is processed similarly to the spectral method. In particular, the referenced analytical signal is sampled at time synchronized points on the T wave for a collection of 128 beats (step 645), and a time series is created for each point on the collection of T waves (step 650). As in the spectral method, a time series is created by measuring, for each of the 128 beats, the T-wave level at a fixed point relative to the QRS complex. This process is repeated to create a time series for each point in the T wave.

Next, the time series are processed to reduce noise such as that resulting from baseline wander (step 653). In general, this processing uses other signals, including those corresponding to respiration and impedance, to adaptively remove baseline wander. Techniques for processing the time series are described in more detail in U.S. Pat. No. 5,704, 365, titled "USING RELATED SIGNALS TO REDUCE ECG NOISE," which is incorporated by reference.

A frequency spectrum is then generated for each time series (step 655), and the spectra are averaged to form a composite T-wave alternans spectrum (step 660). Since the T-waves are sampled once per beat for each time series, the spectral value at the Nyquist frequency, i.e. 0.5 cycle per beat, indicates the level of beat-to-beat alternation in the T-wave waveform.

Finally, the alternans power is statistically compared to the noise power to discriminate the beat-to-beat T-wave variation due to abnormal electrical activity of the heart from the random variation due to background noise (step 665). The alternans power is calculated by subtracting the mean power in a reference band used to estimate the background noise level from the power at the Nyquist frequency (0.50 cycle per beat). In one implementation, the reference band includes frequencies from 0.43 to 0.49 and 0.51 to 0.56 cycles per beat. In the same implementation, alternans is considered to be significant if it is at least three times the standard deviation of the noise in the noise reference band.

In general, the technique 600 reduces or eliminates the effects of aliasing. The amount of aliasing depends on the patient's heart rate and reduces as the heart rate increases. For heart rates of primary interest, such as 80 to 120 beats per minute, the sampling frequency is approximately 2 Hz. In the spectral method, this would have meant that any signal component of frequency content over 1 Hz would be a source of aliasing.

Since aliasing is primarily due to the interference between the frequency components at the positive part of the spectrum and those at the negative part of the spectrum from an adjacent period of the spectrum, creation of an analytical signal serves to avoid aliasing. In particular, creation of the analytical signal removes the interfering negative frequency components while scaling the signal to preserve the total signal energy.

An analytical signal is a complex signal. See Proakis J G, Manolakis D G, Digital Signal Processing, Prentice Hall, Upper Saddle River, N.J., 1996, pp. 738–742, which is incorporated by reference. The real part of the complex signal, y, is the original signal, x, and the imaginary part is the Hilbert transform, H(x), of the original signal:

$$y=x+jH(x),$$

where H(x) is the Hilbert Transform of x with the following transfer function.

$$H(\omega) = \begin{cases} -j & \text{for } 0 < \omega \leq +\pi \\ +j & \text{for } -\pi < \omega \leq 0 \end{cases}$$

The Hilbert Transform returns a complex sequence. This sequence is a version of the original real sequence with a 90° phase shift. It has the same amplitude and frequency content as the original real data and includes phase information that depends on the phase of the original data.

The overall transform has the following real transfer function:

$$H_a(\omega) = \begin{cases} 0 & \text{for } -\pi < \omega \leq 0 \\ 1 & \text{for } \omega = 0 \\ 2 & \text{for } 0 < \omega \leq +\pi \end{cases}$$

The analytic signal is characterized as having an asymmetric spectrum with components of negative frequency having been removed. A variety of time domain and frequency domain processing methods and filters that can be used to implement or approximate the analytic signal approach. These methods affect certain frequencies $\omega_n$ of the input signal differently for the positive frequency $+|\omega_n|$ and the corresponding negative frequency $-|\omega_n|$. The result is a signal having an asymmetric spectrum. Examples of suitable processing methods and filters include, but are not limited to, spectral windowing functions and time domain functions which convolve the input signal with a signal whose spectrum is asymmetric. There are a number of techniques that may be used to create suitable functions. These techniques include, but are not limited to, Chebyshev approximation, FIR or IIR filter design, windowing techniques, recursive design techniques, and inverse Z-transform techniques.

Figure 7A:
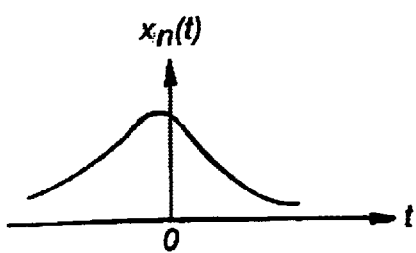
FIGS. 7A and 7B are graphs of, respectively, a band-limited signal and the power spectrum of the signal.
Figure 7B:
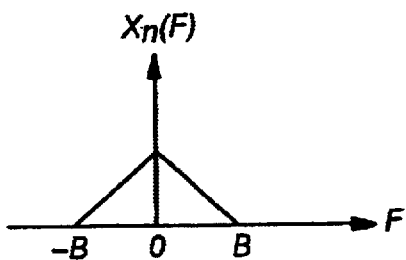
Figure 8:
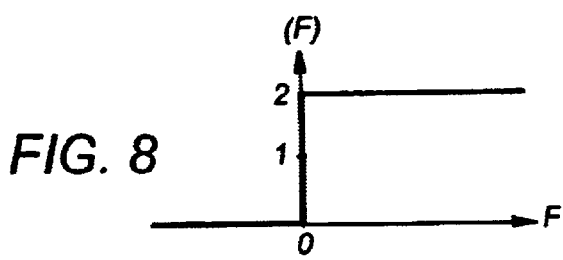
FIG. 8 is a graph of the transfer function of a filter used to generate an analytical signal from a band-limited signal.
Figure 9:
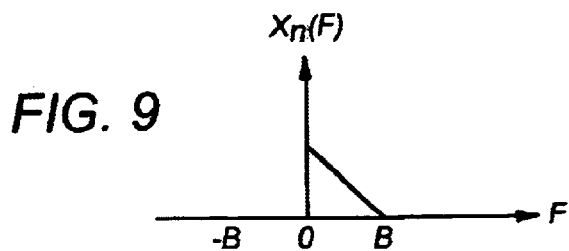
FIG. 9 is a graph of a power spectrum of the analytical signal.
Figure 10A:
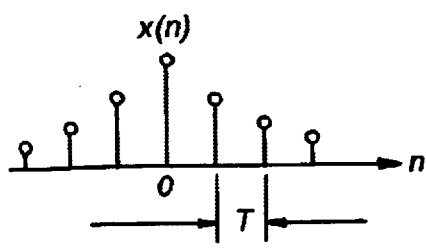
FIGS. 10A and 10B are graphs of, respectively, the analytical signal sampled at a frequency less than twice the frequency of the highest frequency component of the band-limited signal, and the corresponding power spectrum.
Figure 10B:
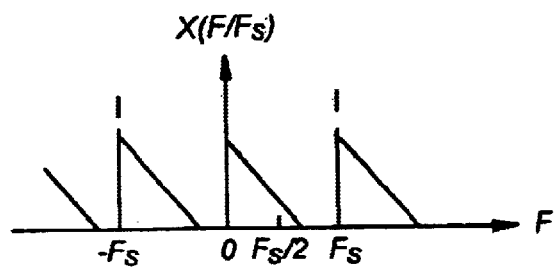

The band-limited signal shown in FIG. 7A has the power spectrum shown in FIG. 7B. When the filter shown in FIG. 8 is applied to the signal of FIG. 7A, an analytical signal having the power spectrum shown in FIG. 9 is created. That signal then may be sampled at a frequency less than twice the bandwidth, as shown in FIG. 10A. For an electrocardiogram signal, by down sampling the signal at T-wave locations, the digital spectrum is still a periodic spectrum with a period of 1/sampling interval, i.e., the heart rate. As shown in FIG. 10B, interference between the positive and negative frequencies is eliminated since the negative part of the spectrum is removed.

This approach allows an accurate measurement of T-wave alternans even when there is colored noise at or close to alternans frequency, such as may occur in treadmill exercise tests. FIGS. 11A and 11B illustrate a comparison between the analytical approach and the existing spectral method. It is evident that the presence of colored noise within the noise band results in an overestimation of alternans power and underestimation of noise power in the spectral method. By contrast, the analytical method provides an accurate estimation of both the alternans and the noise within the noise band.

Other embodiments are within the scope of the following claims.

What is claimed is:

1. A method for measuring alternans in a physiological signal, the method comprising:
   processing the physiological signal to create a processed signal having an asymmetric spectrum; and
   processing the processed signal to measure alternans in the physiologic signal.

2. The method of claim 1 wherein processing the physiological signal to create a processed signal comprises creating the processed signal as an analytical signal.

3. The method of claim 2 wherein creating the processed signal as an analytical signal comprises generating a frequency domain representation of the physiological signal, modifying the frequency domain representation to remove components corresponding to negative frequencies, and generating the analytical signal as a time domain representation of the modified frequency domain representation.

4. The method of claim 3 wherein the physiological signal comprises an electrocardiogram signal.

5. The method of claim 4 wherein the physiological signal comprises an electrocardiogram recorded from a subject during exercise.

6. The method of claim 5 wherein the exercise comprises using an ergometer.

7. The method of claim 5 wherein the exercise comprises using a treadmill.

8. The method of claim 1 wherein processing the processed signal includes sampling the processed signal at a frequency less than or equal to twice a frequency corresponding to alternans.

9. The method of claim 1 wherein processing the processed signal includes processing samples of the signal spaced by intervals greater than or equal to half the period of alternans.

10. The method of claim 1 wherein processing the physiological signal comprises creating an approximation of an analytical signal version of the physiological signal.

11. The method of claim 10 wherein processing the processed signal includes sampling the processed signal at a frequency less than or equal to twice a frequency corresponding to alternans.

12. The method of claim 1 wherein the physiological signal comprises an electrocardiogram signal.

13. The method of claim 12 wherein the physiological signal comprises an electrocardiogram recorded from a subject during exercise.

14. The method of claim 13 wherein the exercise comprises using an ergometer.

15. The method of claim 13 wherein the exercise comprises using a treadmill.

16. The method of claim 1 wherein the physiological signal comprises a physiological signal recorded from a subject during exercise.

17. The method of claim 16 wherein the exercise comprises using an ergometer.

18. The method of claim 16 wherein the exercise comprises using a treadmill.

19. A method for analyzing a band-limited signal, the method comprising:
   producing an analytical signal version of the signal;
   sampling the analytical signal; and
   processing samples of the analytical signal spaced by intervals greater than or equal to half the period of the highest frequency component of the band-limited signal.

20. The method of claim 19 wherein the band-limited signal comprises a physiological signal.

21. The method of claim 20 wherein the physiological signal comprises an electrocardiogram signal.

22. The method of claim 19 wherein processing samples of the analytical signal involves measurement of alternans.

23. The method of claim 19 wherein the band-limited signal is periodic and processing the samples of the analytical signal includes detecting frequency components which are located at or near submultiples of the reciprocal of the period of the band-limited signal.

24. A system for measuring alternans in a physiological signal, the system comprising:
- an input unit configured to receive the physiological signal;
- a processor connected to the input unit and configured to process the physiological signal to create a processed signal having an asymmetric spectrum, and to process the processed signal to generate an indication of alternans in the physiologic signal; and
- an output unit connected to the processor and configured to receive and output the indication of alternans.

25. The system of claim 24 wherein the processor is configured to create the processed signal as an analytical signal.

26. The system of claim 25 wherein the processor is configured to create the processed signal as an analytical signal by generating a frequency domain representation of the physiological signal, modifying the frequency domain representation to remove components corresponding to negative frequencies, and generating the analytical signal as a time domain representation of the modified frequency domain representation.

27. The system of claim 25 wherein the input unit comprises circuitry configured to receive an electrocardiogram signal, the system further comprising an electrode connected to the input unit and configured to produce an electrocardiogram signal.

28. The system of claim 24 wherein the processor is configured to sample the electrocardiogram signal at a frequency of once per beat.

29. The system of claim 24 wherein the processor is configured to sample the processed signal at a frequency less than or equal to twice a frequency corresponding to alternans.

* * * * *